(12) United States Patent
Cottone et al.

(10) Patent No.: US 8,221,482 B2
(45) Date of Patent: Jul. 17, 2012

(54) FLARED OSTIAL ENDOPROSTHESIS AND DELIVERY SYSTEM

(75) Inventors: Robert J. Cottone, Fort Lauderdale, FL (US); Gary J. Becker, Miami, FL (US)

(73) Assignee: OrbusNeich Medical, Inc., Fort Lauderdale, FL (US)

( * ) Notice: Subject to any disclaimer, the term of this patent is extended or adjusted under 35 U.S.C. 154(b) by 1236 days.

(21) Appl. No.: 10/352,328

(22) Filed: Jan. 27, 2003

(65) Prior Publication Data

US 2004/0093058 A1 May 13, 2004

(51) Int. Cl.
*A61F 2/06* (2006.01)
(52) U.S. Cl. ...................................... 623/1.11; 606/108
(58) Field of Classification Search .................. 623/1.11, 623/1.15, 1.36; 606/108, 194, 195, 198
See application file for complete search history.

(56) References Cited

U.S. PATENT DOCUMENTS

| | | | |
|---|---|---|---|
| 5,122,154 A * | 6/1992 | Rhodes ........................ | 623/1.13 |
| 5,549,663 A * | 8/1996 | Cottone, Jr. .................. | 623/1.22 |
| 5,674,276 A * | 10/1997 | Andersen et al. .............. | 623/1.5 |
| 5,683,449 A * | 11/1997 | Marcade ....................... | 128/898 |
| 5,755,774 A * | 5/1998 | Pinchuk ........................ | 623/1.13 |
| 5,913,897 A * | 6/1999 | Corso et al. ................... | 623/1.15 |
| 5,925,061 A * | 7/1999 | Ogi et al. ...................... | 623/1.2 |
| 6,004,347 A * | 12/1999 | McNamara et al. ......... | 623/23.64 |
| 6,117,165 A * | 9/2000 | Becker .......................... | 623/1.15 |
| 6,152,944 A * | 11/2000 | Holman et al. ............... | 623/1.11 |
| 6,168,621 B1 | 1/2001 | Vrba | |
| 6,254,609 B1 | 7/2001 | Vrba et al. | |
| 6,296,661 B1 * | 10/2001 | Davila et al. ................. | 623/1.13 |
| 6,409,755 B1 | 6/2002 | Vrba | |
| 6,517,570 B1 * | 2/2003 | Lau et al. ...................... | 623/1.13 |
| 6,740,113 B2 | 5/2004 | Vrba | |

FOREIGN PATENT DOCUMENTS

| | | |
|---|---|---|
| WO | WO 98/07390 | 2/1998 |
| WO | WO 98/53761 | 12/1998 |
| WO | WO 00/18328 | 4/2000 |
| WO | WO 00/33770 | 6/2000 |
| WO | WO 01/66161 A1 | 9/2001 |

* cited by examiner

*Primary Examiner* — Victor Nguyen
(74) *Attorney, Agent, or Firm* — White & Case LLP

(57) ABSTRACT

An intraluminal endoprosthesis having a conically shaped first end and a tubular shaped balloon-expandable stent for a main body is disclosed. The conically shaped first end may form a flare to the main body and is particularly well suited for in ostium use. The first end is preferably self-expanding and the main body is preferably balloon-expandable. Also disclosed is a delivery device for delivering intraluminal ostial endoprosthetic devices, especially those disclosed herein, to a site for deployment. The delivery device may comprise an over-the-wire system or may comprise a rapid-exchange shuttle system. The self-expanding portion of the endoprosthesis is encapsulated in a sheath or other restraining apparatus on the delivery device. The balloon-expandable stent portion of the endoprosthesis is crimped onto a balloon delivery device. The delivery system and endoprosthesis of the present invention allow the endoprosthesis to be partially expanded and relocated if it is determined that it is not located in the proper location. To aid in positioning, the delivery device may comprise marker bands.

13 Claims, 17 Drawing Sheets

Flared Ostial Stent Deployment

Orbus Flared Ostial Stent (renal artery indication)

Flared Ostial Stent Deployment

Flared Ostial Stent Deployment

Flared Ostial Stent Deployment

Flared Ostial Stent Deployment FIG.8

Flared Ostial Stent Deployment FIG.9

Flared Ostial Stent Deployment

Flared Ostial Stent Deployment inflated_deployed5 deflated_deployed deflated_sheathed

FLARED OSTIAL ENDOPROSTHESIS AND DELIVERY SYSTEM

BACKGROUND OF THE INVENTION

1. Field of the Invention

The present invention relates to intraluminal endoprosthetic devices. In particular, the present invention relates to ostial intraluminal endoprosthetic devices and delivery systems and methods for deploying them.

2. Description of Related Art

Stents are prosthetic devices that are implanted in the lumen of a vessel inside the body to provide support for the wall of the vessel. Typically, stents are implanted within a vessel system to reinforce vessels that are partially occluded, collapsing, weakened, or abnormally dilated. In some cases, stents may be used to address ostial lesions in renal, subclavian, carotid, LCA, RCA, and SVG coronary bypass graft anastomosis sites, as well as in other locations. More generally, stents can be used inside any physiological conduit or duct, including arteries, veins, bile ducts, the urinary tract, alimentary tracts, the tracheobronchial tree, a cerebral aqueduct or the genitourinary system, for example. Stents may be used in both humans and animals.

There are typically two types of stents: self-expanding stents and balloon-expandable stents. Self-expanding stents automatically expand once they are released and assume a deployed, expanded state. A balloon-expandable stent is expanded using an inflatable balloon catheter or other balloon delivery device. The balloon is inflated to plastically deform the stent. Balloon-expandable stents may be implanted by mounting the stent in an unexpanded or crimped state on a balloon segment of a catheter. The catheter, after having the crimped stent placed thereon, is inserted through a puncture in a vessel wall and moved through the vessel until it is positioned in a portion of the vessel that is in need of repair. The stent is then expanded by inflating the balloon catheter against the inside wall of the vessel. The stent is plastically deformed by the inflation of the balloon so that its diameter increases and remains at an increased state. In some situations, the vessel that the stent is implanted into may be dilated by the stent itself when the stent is expanded.

Balloon-expandable stents are more easily and more accurately positioned because they can be expanded slowly, uniformly, and without undue movement axially during placement. A balloon-expandable stent may be moved within a vessel even after it has started to expand. In contrast, self expanding stents are more difficult to position and more difficult to move once they have started to expand. Self expanding stents, while more difficult to align and accurate place within a vessel do have some advantages, particularly when addressing ostial lesions in vessels. Self-expanding stent exert continual outward radial force and form a "pre-determined" shape or diameter. This is particularly useful when trying to address ostial lessions.

SUMMARY OF THE PRESENT INVENTION

The present invention is directed to intraluminal endoprosthetic devices having a flared or conical end region and delivery systems for positioning them within lumens of vessels. In one embodiment, the present invention comprises a balloon-expandable stent coupled with a self-expanding flared region. When the endoprosthesis is deployed, its self-expanding region forms a conical or a flare shape. The self-expanding region is coupled to the balloon-expandable stent with an encapsulating material or membrane. In some embodiments, the encapsulating material covers a portion of both the self-expanding region and the balloon-expandable stent or covers and/or encapsulates both entirely.

The present invention also provides for a delivery system for flared intraluminal ostial endoprosthetic devices. In one embodiment, an intraluminal ostial endoprosthesis is delivered to a site with a delivery apparatus having a distal region. A balloon delivery device is mounted over the distal region of the delivery apparatus so as to encapsulate it, or at least a portion of it. A balloon-expandable region, which is comprised of a balloon-expandable stent, is crimped onto the balloon delivery device. A sheath or retaining device, such as a ring, is mounted over a self-expanding region of the endoprosthesis. The delivery apparatus of the present invention may traverse a guidewire, may be delivered to the site of interest via a rapid-exchange shuttle, or may be an "over-the-wire" type device. In some embodiments, it is desirable to include marker bands on the distal region of the delivery apparatus so the location and/or orientation of the endoprosthesis, which is mounted thereon, may be ascertained during deployment. In one embodiment, the delivery device has three marker bands, a distal marker band, a proximal marker band, and a middle marker band. The distal marker band is the most distal of the three and the proximal is the most proximate of the three.

Once the endoprosthesis is delivered to the general region where it is to be implanted, the balloon device is partially inflated. Often it is necessary to use radiological or other techniques for determining the precise location of the endoprosthesis. If it is not located at a proper location, even in a partially inflated state, it may be repositioned. After it is confirmed that it is in the proper location, the balloon is completely inflated. This inflation plastically deforms the balloon-expandable portion of the endoprosthesis. In one embodiment, as the balloon expands, the sheath begins to pull back from the self-expanding region and the self expanding region deploys to its predetermined size. The delivery balloon is then deflated and the delivery apparatus is removed from the vessel.

In another embodiment, the balloon is inflated and then a capture sheath, ring, or other sutiable restraining apparatus is removed from the endoprosthesis's self-expanding regions. The restraining apparatus may be removed at any time during deployment. In one embodiment, it is removed after the balloon is fully inflated. In other embodiments, it is removed from the self-expanding region before the balloon is inflated or after the balloon is only partially inflated.

DETAILED DESCRIPTION OF THE PRESENT INVENTION

Figure 1:
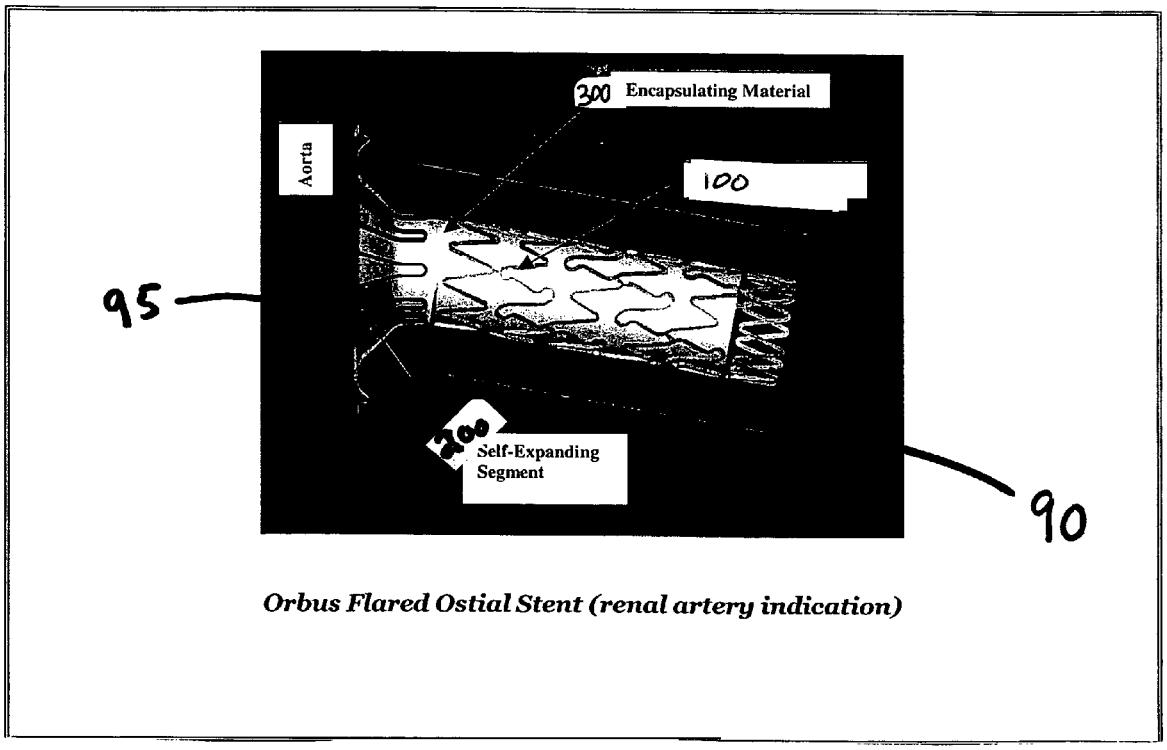
FIG. 1 depicts an endoprosthesis according to the present invention in an "as deployed" view, when used to address a renal arterial indication.
Figure 2A:
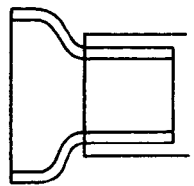
FIGS. 2a-2f depict exemplary flared sections of the endoprosthesis of the present invention.
Figure 2B:
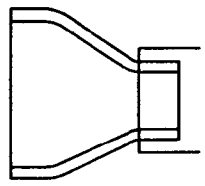
Figure 2C:
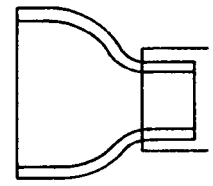
Figure 2D:
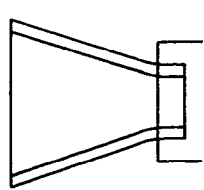
Figure 2E:
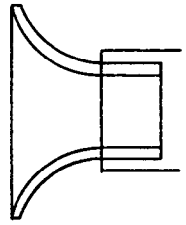
Figure 2F:
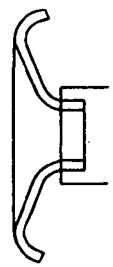
Figure 3A:
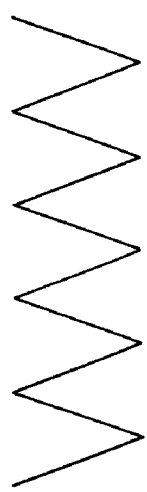
FIGS. 3a-3g depict exemplary web-mesh patterns for the flared portion of the endoprosthesis of the present invention.
Figure 3B:
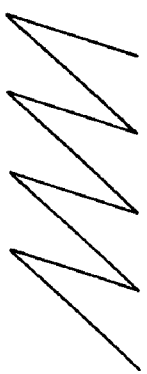
Figure 3C:
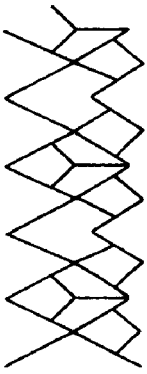
Figure 3D:
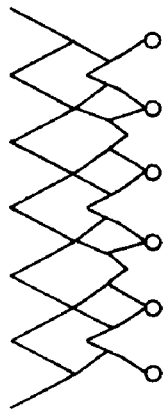
Figure 3E:
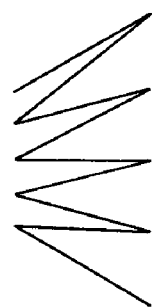
Figure 3F:
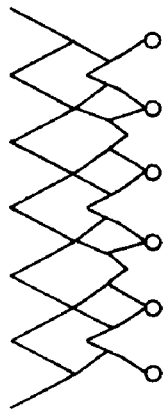
Figure 3G:

The present invention is directed to flared ostial endoprosthetic devices for intraluminal use. As is shown in FIG. 1, which depicts an embodiment of the endoprosthesis according to the present invention when it is deployed in a renal artery 90 branching from an aorta 95, the endoprosthesis may have a balloon-expandable stent region 100 and a self-expanding end-region 200, wherein when the endoprosthesis is deployed, the self-expanding region assumes a flared state. The balloon-expandable stent region preferably has a design that allows for a high stent-to-vessel ratio. In some embodiments, the balloon-expandable stent region 100 will comprise a plurality of helical segments and preferably has a geometry that allows the balloon-expandable stent region to be crimped onto a delivery device. Numerous designs are known in the art and may be used for the balloon-expanding region. For example co-pending applications Ser. No. 10/014,705 to Addonizio et al (Dec. 11, 2001) and provisional application 60/267,778 to Pazienza et al (Feb. 2, 2001) disclose designs well-suited for use in the balloon-expandable region. Both provide for stents having high stent-to-vessel ratios and both employ a plurality of helical segments that expand circumferentially when the stent is expanded by a balloon device. Other balloon-expandable stent designs, which are well-known in the art, may also be used.

In some embodiments, it may be desirable for one end of the balloon-expandable stent region to have a square edge 110. (See FIG. 1). Often an endzone having a square edge may be added to the balloon-expandable region. In some cases, it may be desirable to add a transition region to the balloon-expandable stent region before the square end. Struts or other structural elements may be used to connect the endzone to the rest of the balloon-expandable region.

Figures 4A, 4B:
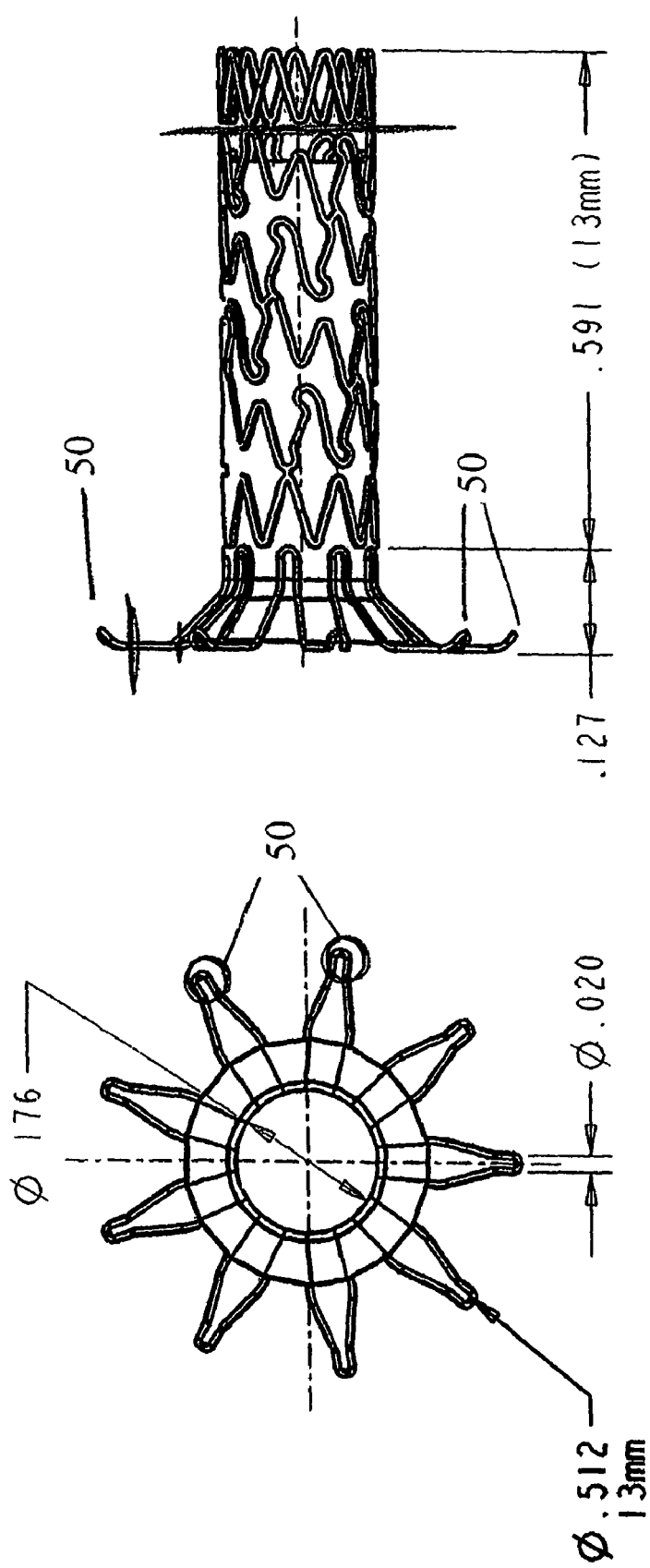
FIGS. 4a-4b illustrate the web-mesh pattern of a support structure for one embodiment of the present invention.

The self-expanding region 200 may be manufactured from NiTi, SST spring steel, polymers, shape memory material, or other suitable stent material and when released from a restraining apparatus assumes a pre-determined shape and size. When expanded, the self-expanding region 200 preferably has a generally flared or generally conical shape and may take many forms including, but not limited to, those shown in FIGS. 2a-2f. The self expanding region 200 may be comprised of a web-mesh pattern taking many forms, including, but not limited to, those shown in FIGS. 3a-g. In some embodiments, compound angle geometry with hooks at the flared self-expanding section may be used to improve contact with vasculature and remodeling of ostial branches. (See also, for example, FIGS. 4a and 4b, in particular elements 50).

As is shown in FIG. 1, the self-expanding region 200 is coupled to the balloon-expandable stent region 100 with an encapsulating membrane 300. In some embodiments, the membrane 300 partially or completely covers both the self-expanding region 200 and the balloon-expanding region 100. The membrane 300 is preferably manufactured from balloon-expandable or plastically deformable material, such as PTFE, fluoropolymer, polyvinyl alcohol (PVA), cross-linked hydrogel, or other suitable material. In an embodiment of the present invention, the material comprising the membrane is sheer. In some embodiments, a segment of, or the entirety of, the encapsulating membrane 300 is pre-deployed into the self-expanding segment shape prior to assembly. The membrane is also used to uniformly remodel atherosclerotic plaques and keep this material from protruding through the stent struts and end region struts and filaments.

The endoprosthesis of the present invention may also act as a drug delivery system. In one embodiment of the present invention, an erodible matrix may be used to act as a platform for drug delivery. The erodible matrix may be composed of an erodible polymer system that is biocompatible. Among the numerous useful drugs that may be delivered by the graft platform described herein are anti-restenosis drugs.

Figure 5:
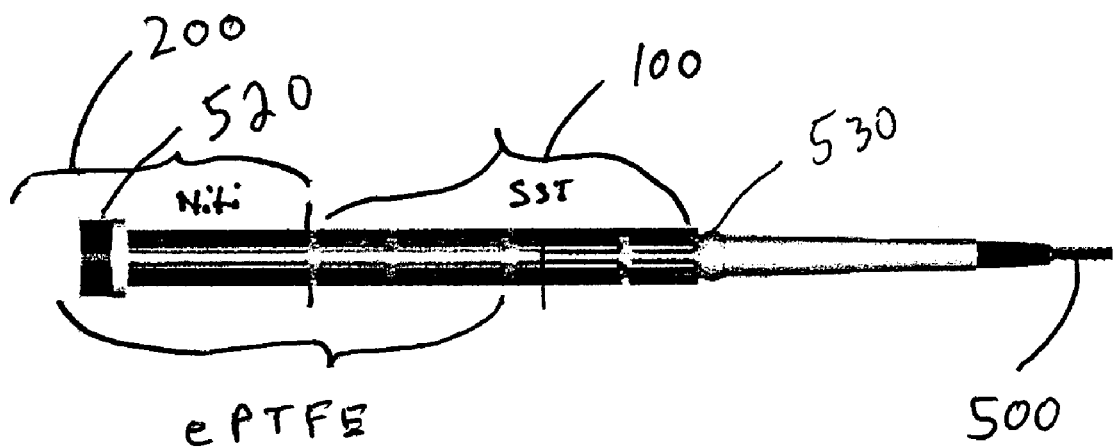
FIG. 5 illustrates an endoprosthesis according to the present invention after it has been mounted on a delivery device according to the present invention.
Figure 6:
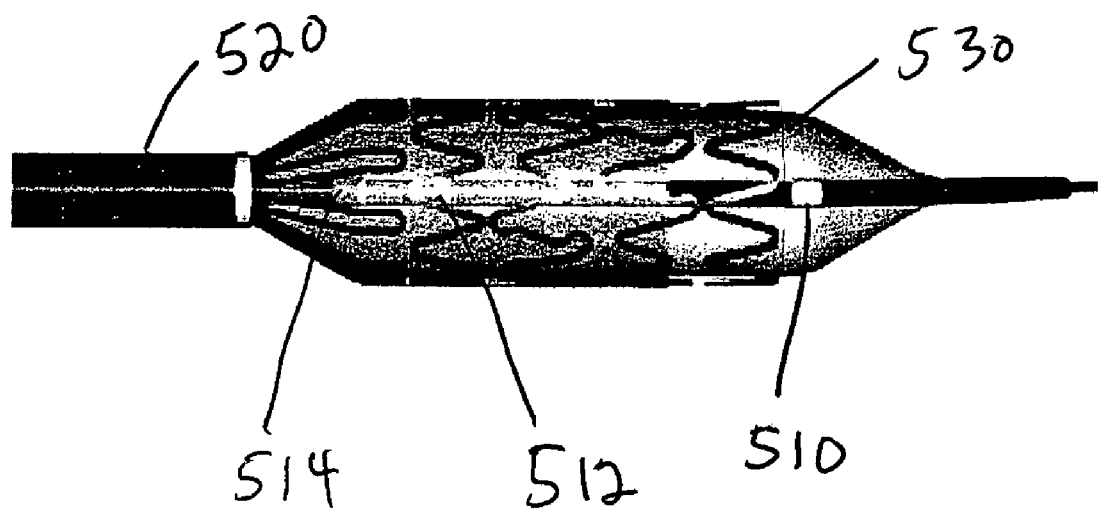
FIGS. 6-9 illustrate the use of the delivery device in deploying an ostial intraluminal endoprosthesis.

The present invention also provides a delivery system for intraluminal ostial endoprosthetic devices. The delivery system may comprise an over-the-wire delivery apparatus or a rapid exhange shuttle system. If an over-the-wire system is used, the delivery apparatus may traverse over a guide wire 500 (e.g., a 0.010- to 0.038-inch wire) to a site for deployment. (See e.g. FIG. 5). As is shown in FIG. 6, marker bands 510, 512, 514 on the delivery apparatus indicate the deployment location of a segment of the device in a vasculature. The end result is that the endoprosthesis is delivered to a lesion site.

In one embodiment, as is shown in FIGS. 5-9, the delivery system of the present invention employs a pull-back sheath 520, which is a tubular segment of a pull-back or restraining system that retains the self-expanding segment 200 from premature deployment. This also allows for precise deployment of the entire device at an ostium. A ring or other suitable restraining apparatus may be used instead of or in addition to the sheath 520.

Figure 7:
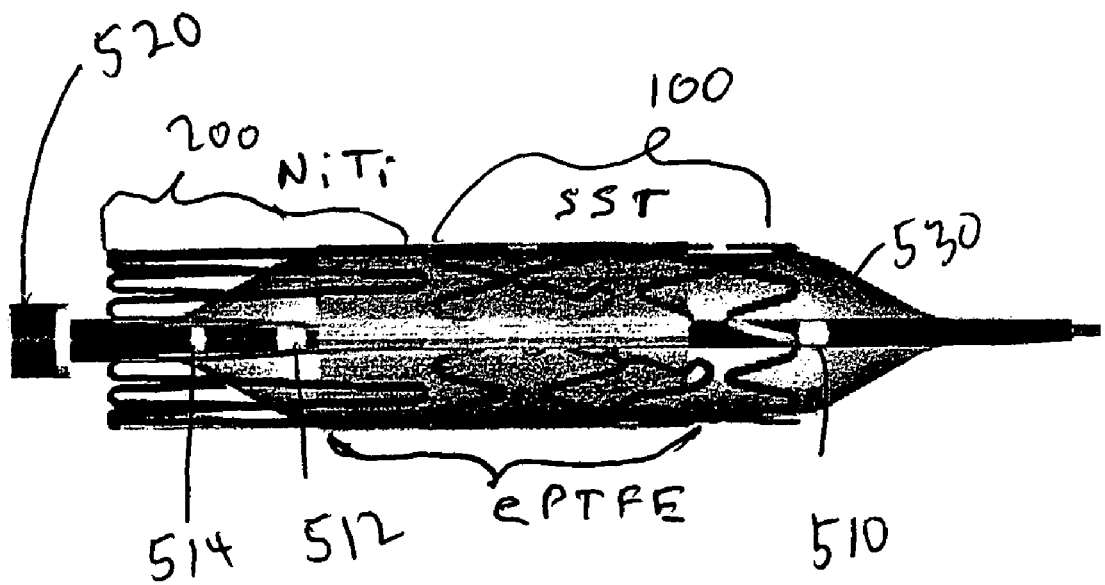
Figure 8:
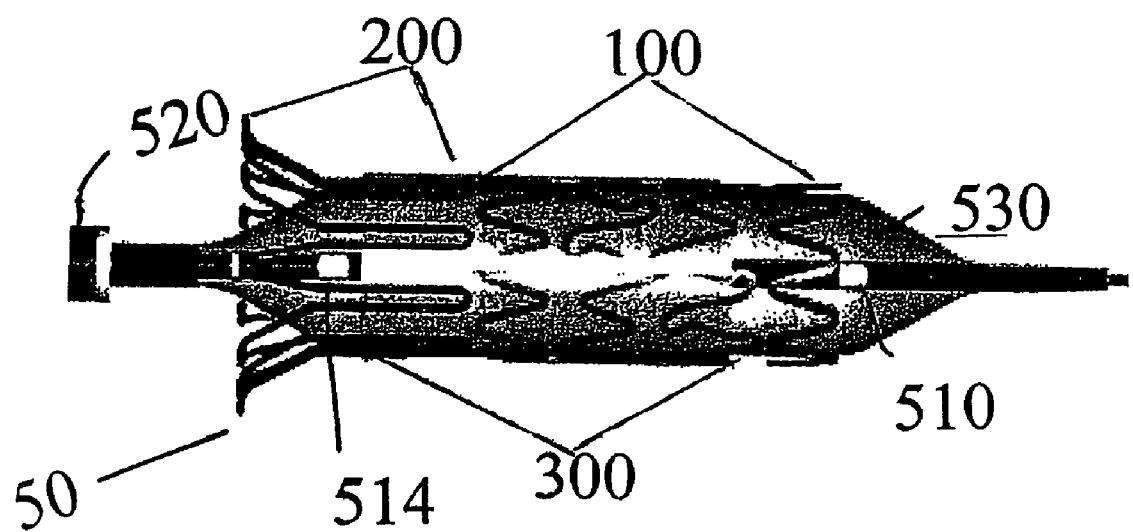
Figure 9:
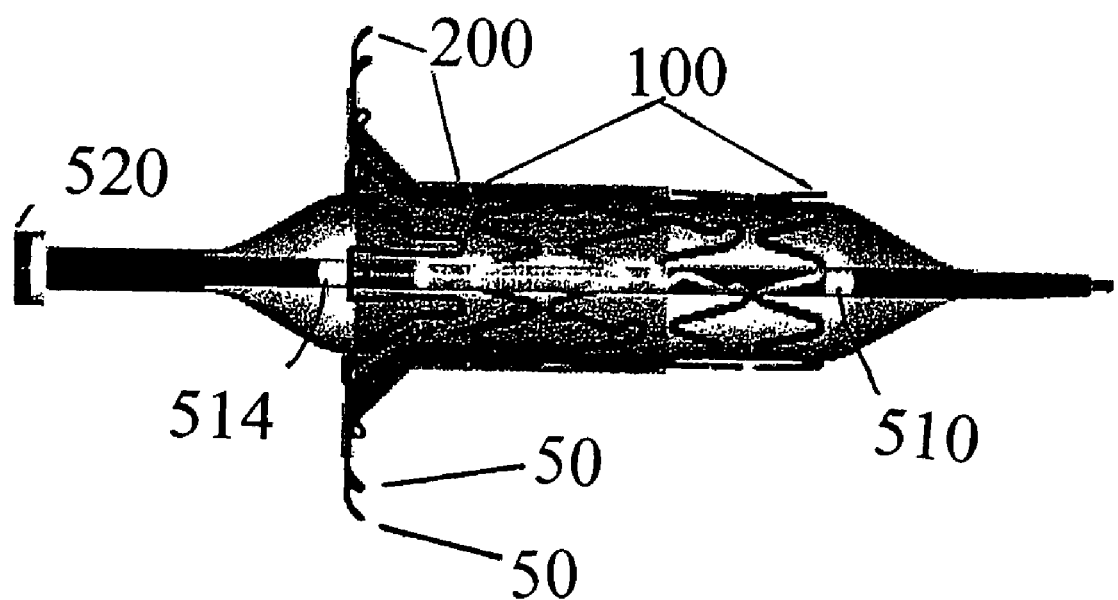
Figure 10:
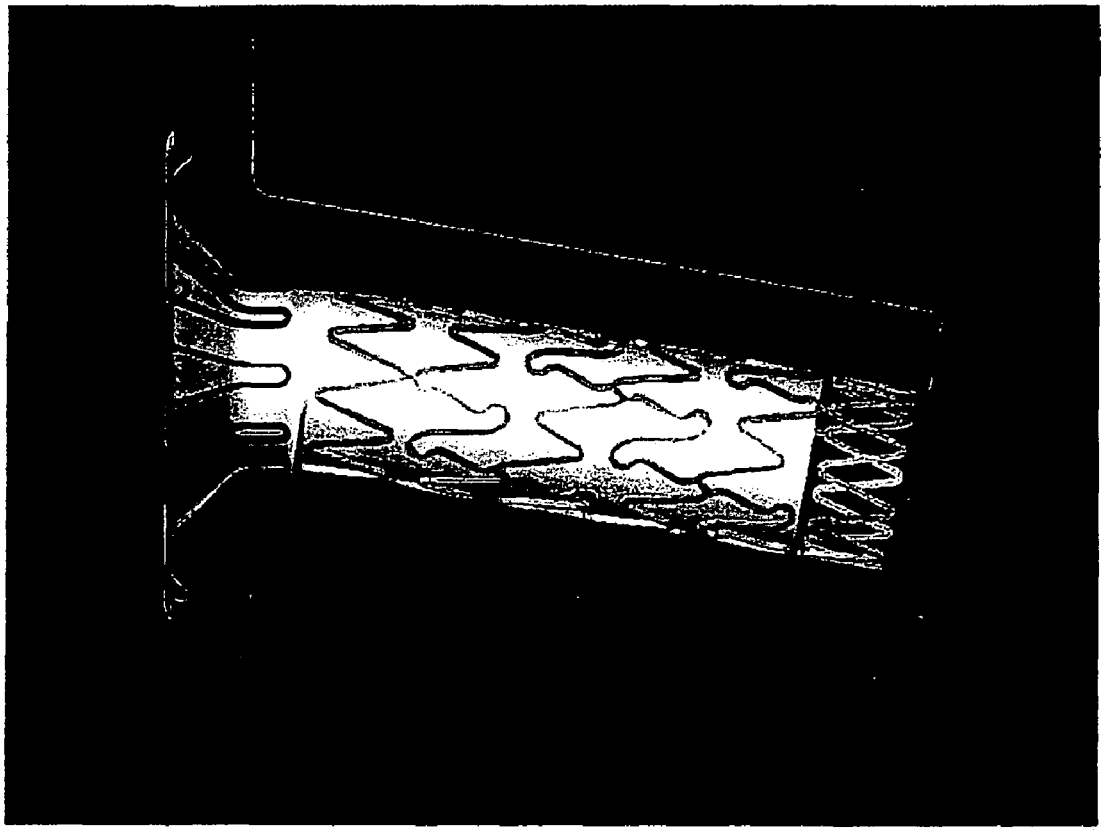
FIGS. 10 and 11 illustrate the endoprosthesis of the present invention after it has been deployed at an ostium.
Figure 11:
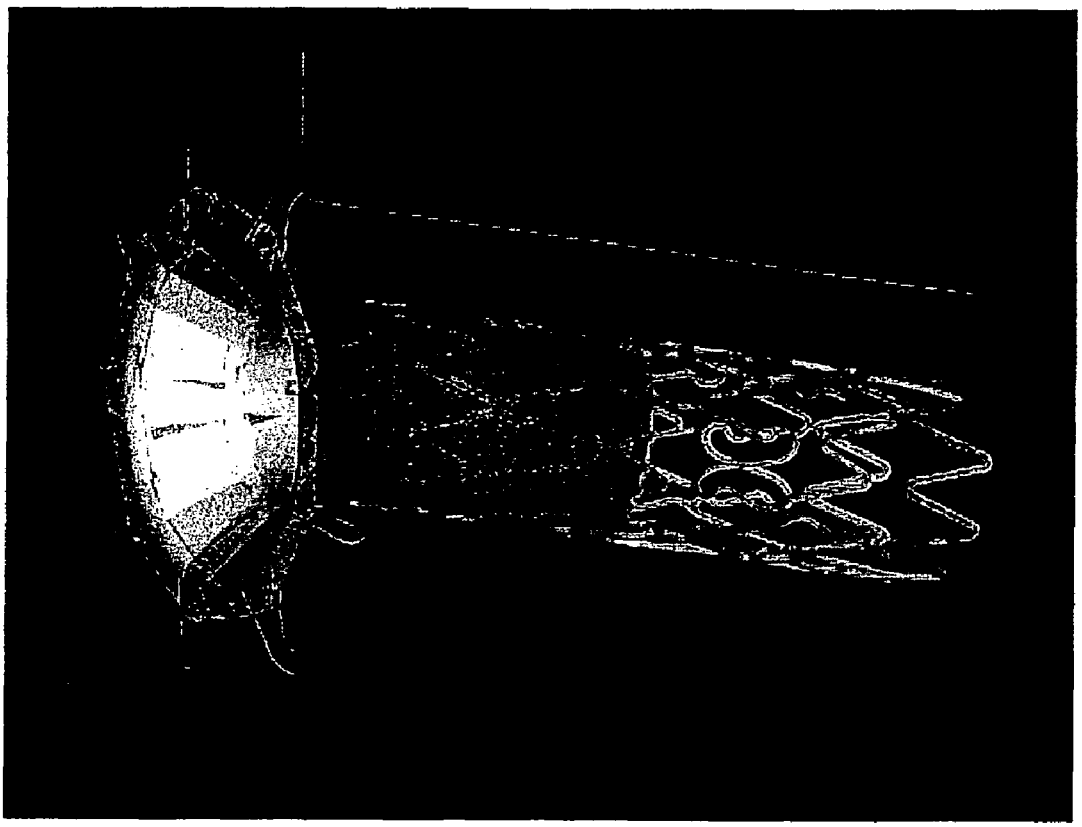
Figure 12:
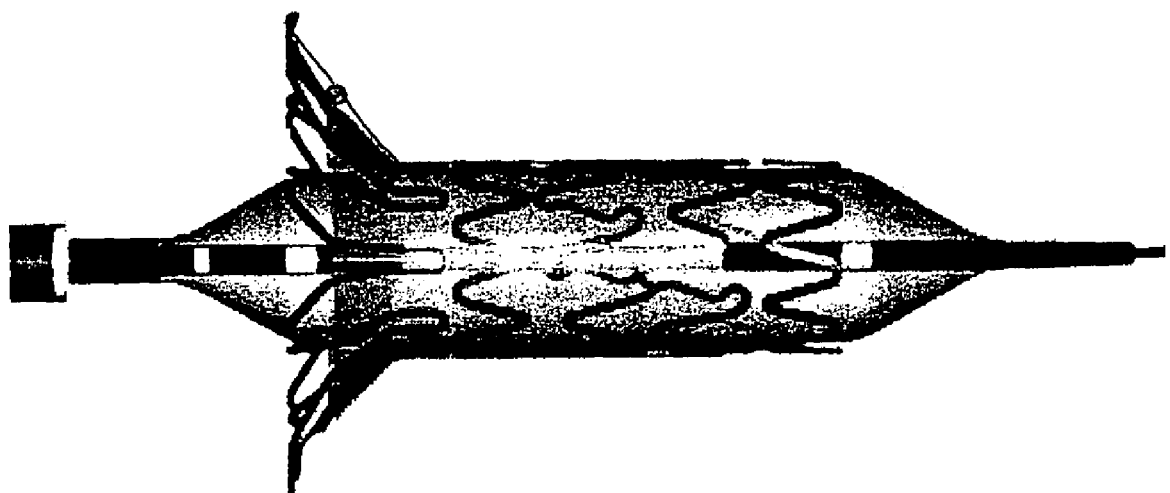
FIGS. 12-17 illustrate various aspects of various embodiments of the endoprosthetic devices, the delivery devices, and the methods of deploying the endoprosthetic devices of the present invention.
Figure 13:
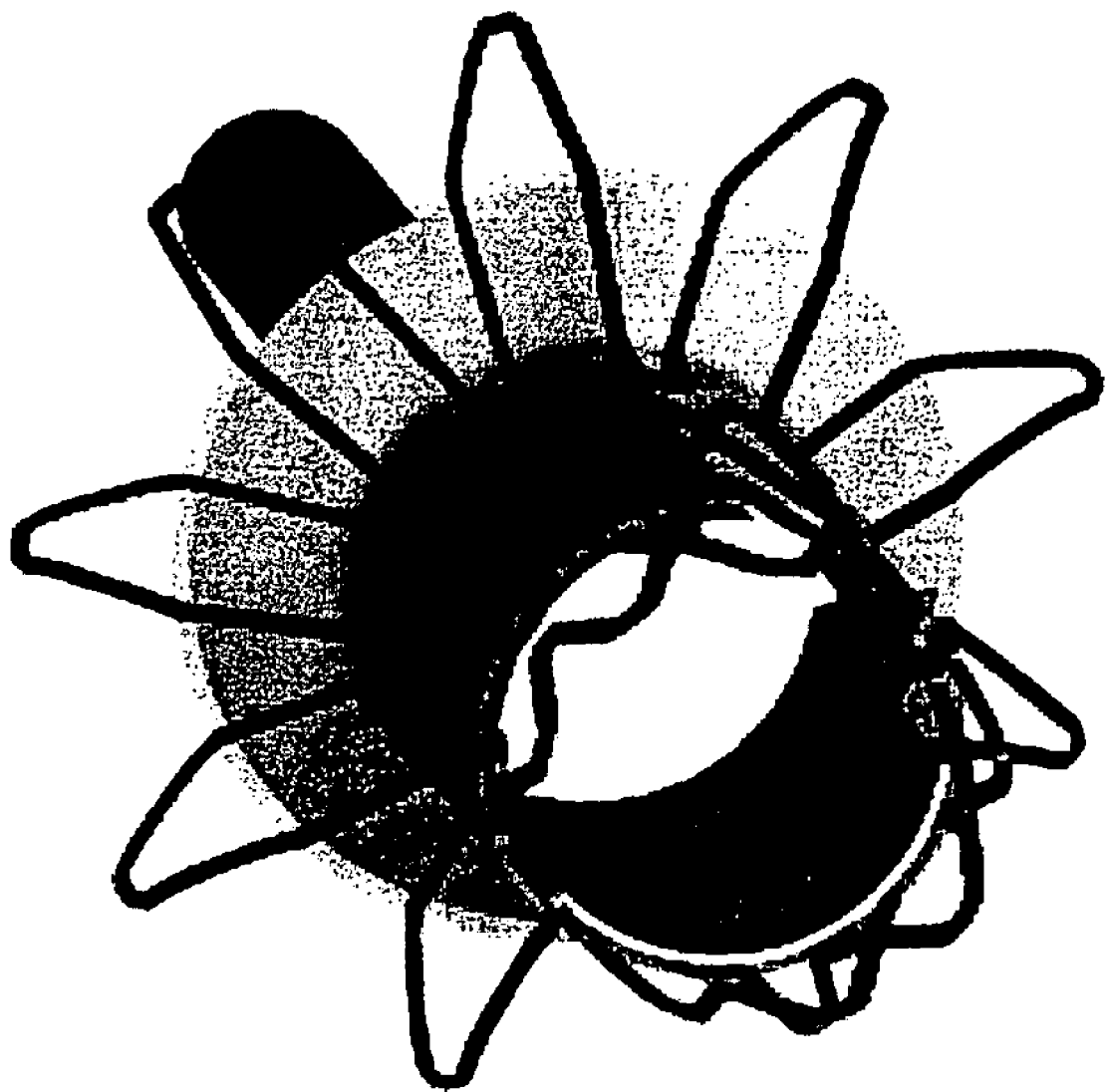
Figure 14:
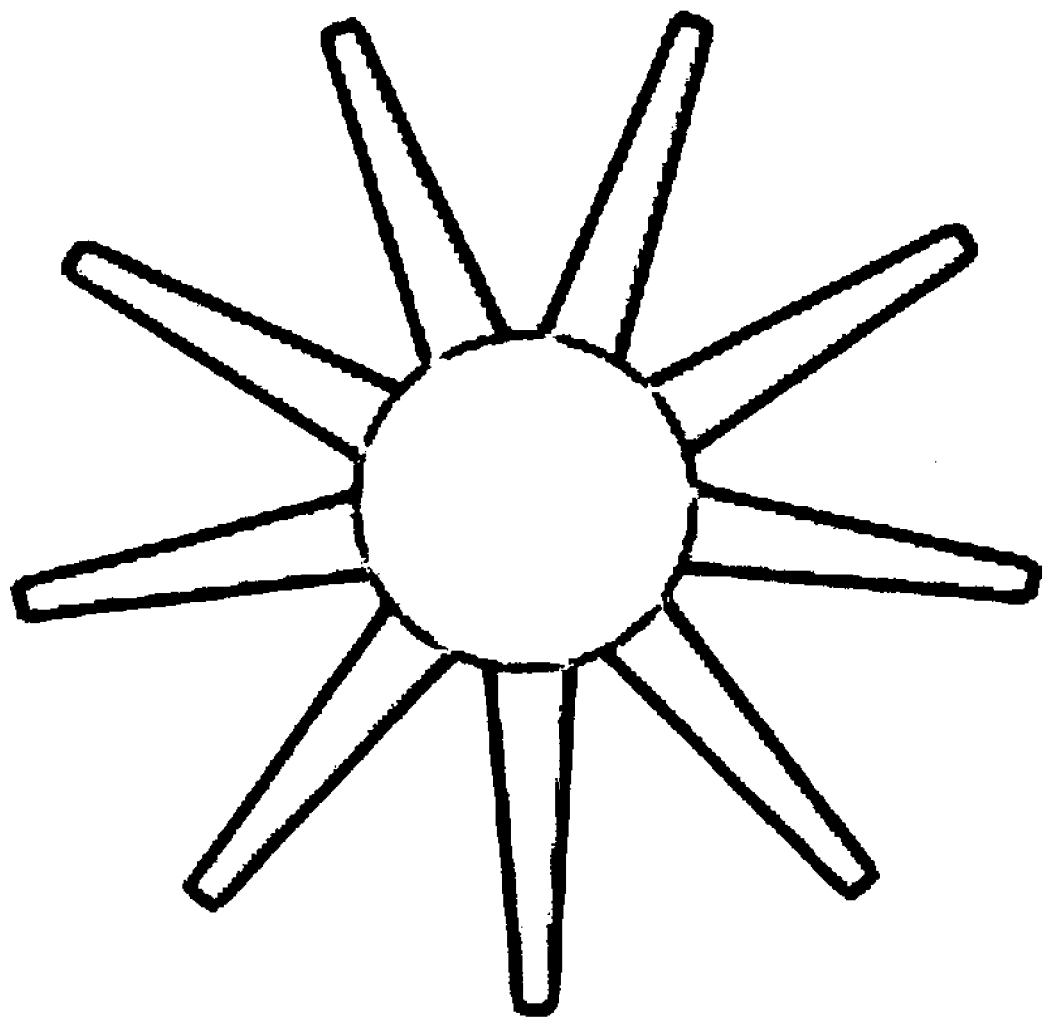
Figure 15:
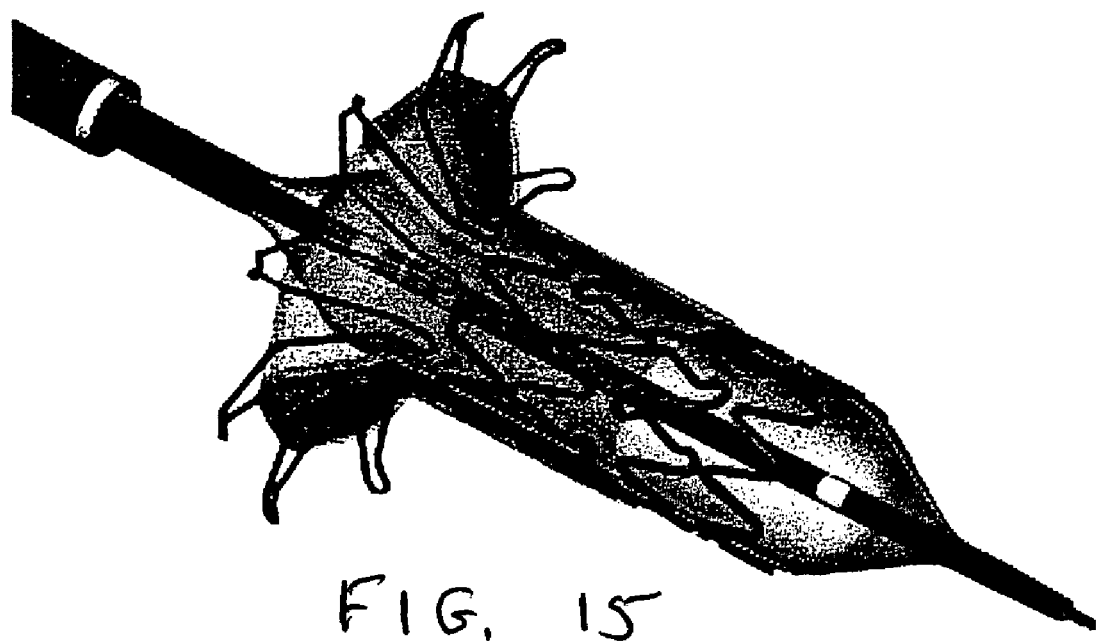
Figure 16:
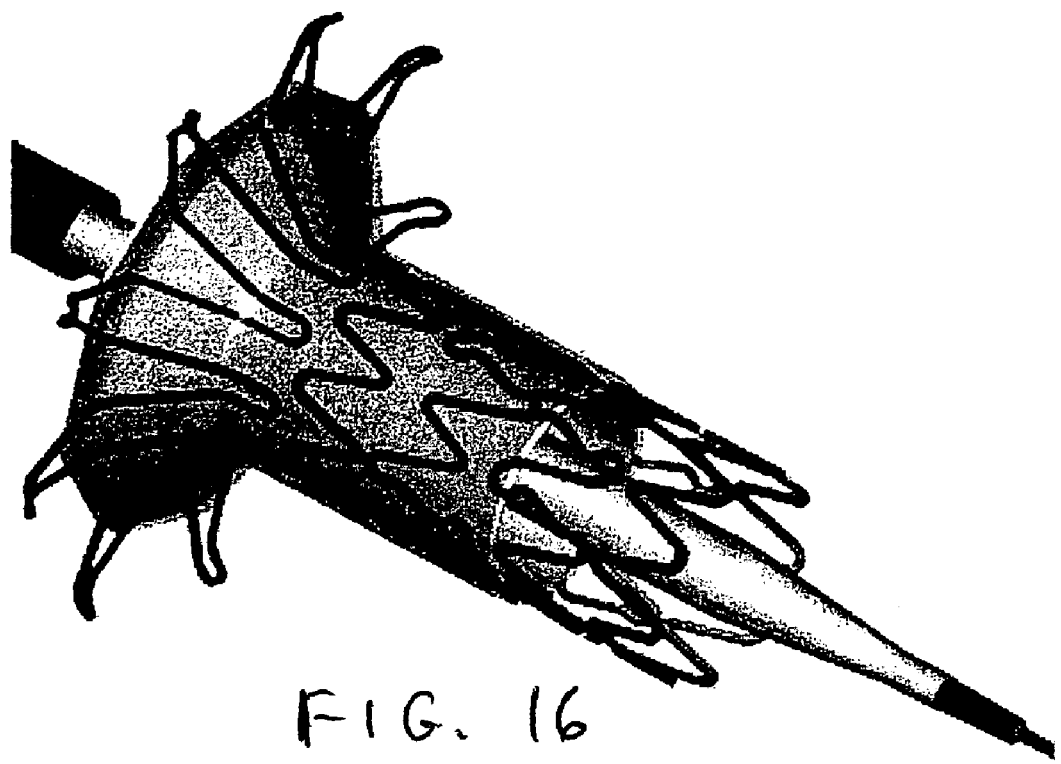
Figure 17:
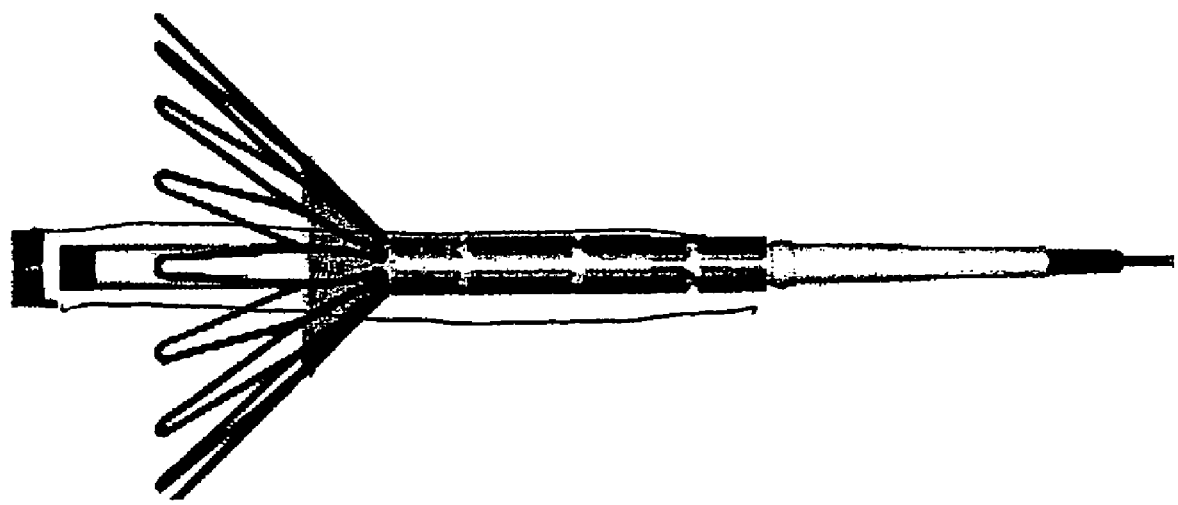

The balloon-expandable stent region 100 of an intraluminal ostial endoprosthesis is mounted on a balloon delivery device 530. As is shown in FIG. 6, as the balloon begins to inflate, the balloon-expandable segment begins to deploy. As the balloon 530 inflates, the self-expanding region 200 begins to pull out of the pull-back sheath 520. As is shown in FIG. 7, by the time the balloon-expanding stent region 100 is fully deployed, the self-expanding region 200 exits the pull-back sheath 520. The self-expanding region 200 begins elastic deformation to a predetermined size. (See FIGS. 8 and 9). As can also be seen in FIGS. 8 and 9, the ends of the flared portion have hooks 50. The balloon is then deflated and the delivery apparatus is removed. The result is that the intraluminal endoprosthesis is anchored into the ostium via the hooks at the end of the flared region as shown in FIGS. 10 and 11.

While, in the embodiment described above, the self-expanding region may automatically exit a restraining apparatus after the balloon-expandable stent portion is expanded to a certain point, it may be desirable for the self-expanding segment to remain restrained in a sheath, ring, or other suitable restraining means until the implanting medical professional desires to allow it to self expand. Thus, in some embodiments, an affirmative action, such as removing the restraining means, must be taken before the self-expanding portion self expands.

The present invention allows for location of the delivery apparatus and the intraluminal endoprosthesis to be obtained and relocated if necessary, even after partial inflation of the balloon-expandable portion of the stent 100.

FIGS. 12-17 clearly depict additional details or provide a different perspective of exemplary embodiments of the present invention and are included herein for illustrative purposes and are not in any way intended to limit the scope of the present invention.

What is claimed is:

1. An intraluminal endoprosthesis comprising:
a first component that is a self-expanding stent, the self-expanding-stent component, when expanded, having a flared portion;
a second component, separated from the first component, that is a balloon-expandable stent; and
a connecting membrane at least partially covering the self-expanding-stent component and the balloon-expandable-stent component and thereby providing a connection between the separate balloon-expandable-stent component and the self-expanding-stent component; wherein, when it is deployed, the self expanding stent component has an outer edge with a radius greater than the expanded radius of the balloon expandable stent component; and wherein the outer end of the self expanding stent component forms hooks.

2. The endoprosthesis of claim 1, wherein the membrane acts as a drug delivery platform.

3. The endoprosthesis of claim 1, wherein exposed sections thereof act as a delivery platform for therapeutic agents.

4. The endoprosthesis of claim 1, wherein the membrane is a fluoropolymer.

5. The endoprosthesis of claim 1, wherein the membrane is erodible.

6. The endoprosthesis of claim 1, wherein the membrane is manufactured from PTFE.

7. The endoprosthesis of claim 1, wherein the self-expanding-stent component is manufactured from NiTi.

8. The endoprosthesis of claim 1, wherein the self-expanding-stent component is manufactured from spring stainless steel.

9. The endoprosthesis of claim 1, wherein the balloon-expandable-stent component comprises a plurality of helical segments.

10. An intraluminal endoprosthetic device comprising:
a first, self-expanding end, the self-expanding end forming a generally cone-shaped portion when the endoprosthesis is deployed;
a second end having a square edge;
a tubular balloon-expandable stent body disposed between the second end and the first, self-expanding end and separated from the first end; and
an encapsulating material that serves to connect the first, self-expanding end and the separate balloon-expandable stent body to each other; wherein the first self expanding end has a flared portion; wherein the flared portion forms hooks.

11. The endoprosthesis of claim 10, further comprising a transition region between the stent body and the square end.

12. The endoprosthesis of claim 10, wherein the hooks form compound angles.

13. The endoprosthesis of claim 10, wherein the encapsulated portion of the self-expanding end is formed prior to mounting the endoprosthesis in a delivery catheter.

* * * * *

UNITED STATES PATENT AND TRADEMARK OFFICE
CERTIFICATE OF CORRECTION

| | |
|---|---|
| PATENT NO. | : 8,221,482 B2 |
| APPLICATION NO. | : 10/352328 |
| DATED | : July 17, 2012 |
| INVENTOR(S) | : Robert J. Cottone et al. |

It is certified that error appears in the above-identified patent and that said Letters Patent is hereby corrected as shown below:

On the title page, between section INID Code (65) and section INID Code (51), insert the following new section INID Code (60):

--(60) Related U.S. Application Data

Provisional application No. 60/352,386, filed on January 28, 2002--

Signed and Sealed this
Twenty-seventh Day of November, 2012

David J. Kappos
*Director of the United States Patent and Trademark Office*